United States Patent [19]

Arlt

[11] 4,435,597
[45] Mar. 6, 1984

[54] PREPARATION OF CARONALDEHYDE ACID AND DERIVATIVES THEREOF

[75] Inventor: Dieter Arlt, Cologne, Fed. Rep. of Germany

[73] Assignee: Bayer Aktiengesellschaft, Leverkusen, Fed. Rep. of Germany

[21] Appl. No.: 355,034

[22] Filed: Mar. 5, 1982

[30] Foreign Application Priority Data

Mar. 26, 1981 [DE] Fed. Rep. of Germany ....... 3111849

[51] Int. Cl.³ ............................................. C07C 51/04
[52] U.S. Cl. .................................. 562/506; 260/501.1
[58] Field of Search ...................... 562/506; 260/501.1

[56] References Cited

FOREIGN PATENT DOCUMENTS 18533  4/1980  European Pat. Off. .
21114  1/1981  European Pat. Off. .
2376119 7/1978 France .

OTHER PUBLICATIONS

Journal of Organic Chemistry, vol. 41,11/5/76, pp. 885–887, Cesare Ferri, "Reaktionen der Organischen Synthese", 1978, p. 202.

*Primary Examiner*—Michael L. Shippen
*Attorney, Agent, or Firm*—Sprung, Horn, Kramer & Woods

[57] ABSTRACT

A process for the preparation of caronaldehyde acid or a derivative thereof of the formula

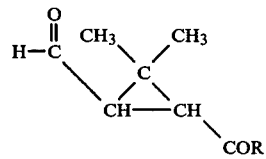

in which
R is O⁻Me⁺, or OH, and
Me⁺ is an equivalent of an alkali metal, alkaline earth metal or ammonium cation, comprising reacting a 2-halogeno-3,3-dimethyl-5,5-dichloropentanoic acid halide of the formula

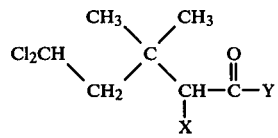

wherein X and Y each independently is a halogen atom, with a base in the presence of water.

5 Claims, No Drawings

PREPARATION OF CARONALDEHYDE ACID AND DERIVATIVES THEREOF

The present invention relates to an unobvious process for the preparation of caronaldehyde acid and certain derivatives thereof.

Various processes for the preparation of caronaldehyde acids have already been disclosed, for example by partial reduction of cyclopropanedicarboxylic acid half-esters with diborane or sodium borohydride to give the hydroxymethyl-cyclopropanecarboxylic acid ester, which is then oxidized with chromic acid in pyridine to give caronaldehyde acid. However, the process is very expensive since the starting materials used are not readily obtainable (see DE-OS (German Published Specification) No. 2,758,624).

Another process uses ethyl 4,5-epoxy-3,3-dimethyl-pentanoate as the starting compound, which is reacted with lithium-diethylamide, in absolute aprotic solvents, to give ethyl 2-hydroxymethyl-3,3-dimethyl-cyclopropanecarboxylate, which is then oxidized with chromic acid in pyridine to give the caronaldehyde acid. This process also uses starting materials which are expensive and not readily available (see J. H. Babler et. al. J. Org. Chem. 41 page 885 et seq. (1976)).

The present invention now provides a process for the preparation of caronaldehyde acid or a derivative thereof of the general formula

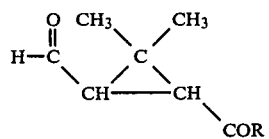

wherein
R represents O⁻Me⁺, or OH, and
Me⁺ represents an equivalent of an alkali metal, alkaline earth metal or ammonium cation, characterized in that a 2-halogeno-3,3-dimethyl-5,5-dichloro-pentanoic acid halide of the general formula

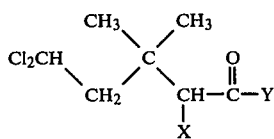

wherein
X and Y independently of each other represent a halogen atom, is reacted with a base in the presence of water, and, if required, the acid is then liberated.

The present invention allows caronaldehyde acid to be obtained by a process which by-passes the stage of formation of cyclopropanedicarboxylic acids. In the process of the present invention, the course of the reaction, with the formation of the aldehyde group, was surprising. Thus, it was to have been expected, according to C. Ferri, Reaktionen der organischen Synthese (Reactions of Organic Synthesis) J. Thieme Verlag 1978 page 202, that a nonactivated aliphatic dichloromethyl compound would split off hydrogen chloride, with the formation of a double bond.

The reaction according to the invention can be illustrated, by way of example, by the following equation:

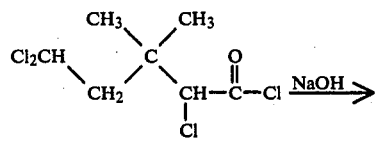

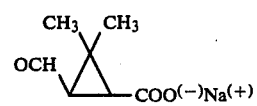

The 2-halogeno-3,3-dimethyl-5,5-dichloro-pentanoic acid halides used as the starting materials are new. Those novel starting materials are described and claimed in application Ser. No. 355,042, filed Mar. 5, 1982, now pending, corresponding to German patent application No. P. 31 11 848.8 (Le A 20 909). They are obtained by a process in which 1,1,1,3-tetrachloro-3-methyl-butane is added onto vinyl chloride, in the presence of Friedel-Krafts catalysts, with the simultaneous elimination of hydrogen chloride, and the vinylidene chloride formed is halogenated in the presence of strong oxygen-containing acids. This reaction can be represented by the following equations:

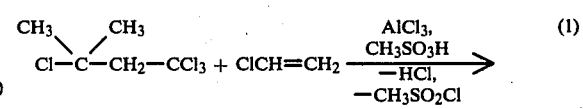

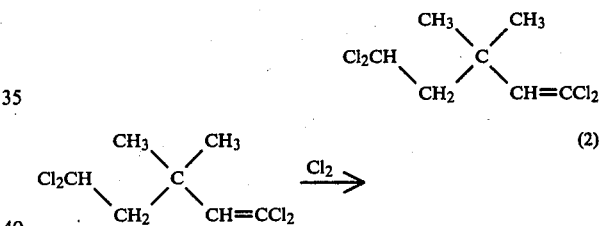

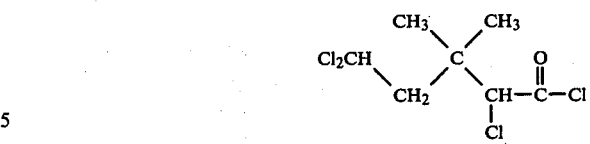

The reaction according to the invention is carried out in the presence of a customary base, such as an alkali metal hydroxide, alkaline earth metal hydroxide, tertiary amine, alkali metal carbonate or alkaline earth metal carbonate.

Water is preferably used as the sole diluent. The reaction can also be carried out in water-containing water-immiscible solvents, such as aliphatic or aromatic hydrocarbons, or ethers (for example tetrahydrofuran). Customary phase transfer catalysts, such as tetralkylammonium hydroxides, can be added as catalysts. The reaction is carried out at a temperature between 80° and 120° C., preferably at a temperature above 90° C.

The reaction is generally carried out under normal pressure or under slightly elevated pressure. The base is generally employed in an equimolar quantity, or if appropriate in an excess of up to 10%.

The working-up is effected in a customary manner. If the acid is to be isolated, the salt solution is acidified and the caronaldehyde acid is extracted. It can be purified by distillation. However, the salt solution can also be reacted with dimethyl sulphate or diethyl sulphate to give the corresponding ester.

The example which follows merely serve to illustrate the process according to the present invention and a process for the production of the starting material therefor.

EXAMPLE (a) 75 g of vinyl chloride were introduced into a solution of 15 g of AlCl$_3$ in 1,000 ml of methylene chloride at −20° C., and 500 g of 1,3,3,3-tetrachloro-1,1-dimethylpropane and a further 105 g of vinyl chloride were then simultaneously metered into the reaction solution during the course of 180 minutes. The reaction mixture was thereafter allowed to react further for 180 minutes at −10° C., and 1,000 ml of water were then added to the solution. After the separation, the aqueous phase was extracted several times with methylene chloride, and the combined organic phases were dried with zeolite and were fractionally distilled. 230 g of the starting material of the boiling point range 32° to 37° C./0.1 mm Hg and 270 g of 1,1,5,5-tetrachloro-3,3-dimethylpent-1-ene of the boiling point range 72° to 76° C./0.15 mm Hg were obtained. This result corresponds to a conversion of 54% with a selectivity of 88%.

(b) 182 g of 1,1,5,5-tetrachloro-3,3-dimethyl-pent-1-ene obtained as described in (a) were dissolved in 400 ml of methanesulphonic acid. 80 g of chlorine were introduced at 10° to 20° C. (cooling with water). The reaction was allowed to continue until a sample, which was obtained by extracting the reaction mixture with hexane, showed no IR absorption at 1,610 cm$^{-1}$. The complete reaction solution was then extracted with hexane. 156 g (=89% of theory) of 2,5,5-trichloro-3,3-dimethylpentanoic acid chloride of boiling point range 92° to 95° C./0.12 mm Hg were obtained from the hexane phase by vacuum distillation, after expelling the hexane.

(c) 100 ml of water were initially introduced into a stirred vessel and heated to 100° C. 63 g (0.25 mol) of 2,5,5-trichloro-3,3-dimethylpentanoic acid chloride and a solution of 58 g of NaOH in 100 ml of water were then simultaneously added dropwise, the pH being monitored, at such a rate that a pH value in the range of 9 to 10 was maintained. The reaction had ended after 30 minutes. The reaction solution was cooled to 20° C., adjusted to pH 2 using hydrochloric acid, and extracted with dichloromethane. After the solvent had been expelled, 36 g of crude acid were obtained, and, after distillation in vacuo, 29.6 g (=83.4%) of pure trans-3-formyl-2,2-dimethylcyclopropane-1-carboxylic acid, boiling point 125–130/0.5 mm Hg, were obtained.

$^1$H-NMR: δ=1.3 (s, 3H) 1.35 (s, 3H) 2.46 (m, 2H) 9.55 (α, split, 1H), 10.95 (s, 1H) ppm.

It will be appreciated that the instant specification and examples are set forth by way of illustration and not limitation, and that various modifications and changes may be made without departing from the spirit and scope of the present invention.

I claim:

1. A process for the preparation of caronaldehyde acid or a derivative thereof of the formula

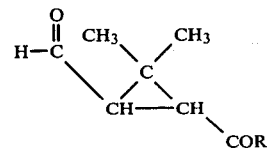

in which
R is O$^-$Me$^+$, and
Me$^+$ is an equivalent of an alkali metal, alkaline earth metal or ammonium cation, comprising reacting a 2-halogeno-3,3-dimethyl-5,5-dichloropentanoic acid halide of the formula

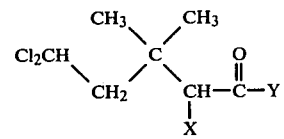

wherein X and Y each independently is a halogen atom, with a base selected from the group consisting of an alkali metal hydroxide, alkaline earth metal hydroxide, tertiary amine, alkali metal carbonate and alkaline earth metal carbonate in the presence of water.

2. A process according to claim 1, wherein the reaction is carried out in water as the sole diluent.

3. A process according to claim 1, wherein the reaction is carried out at a temperature between about 80° and 120° C.

4. A process according to claim 2, wherein the reaction is carried out at a temperature above 90° C.

5. A process for the preparation of caronaldehyde acid of the formula

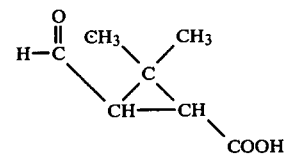

comprising reacting a 2-halogeno-3,3-dimethyl-5,5-dichloropentanoic acid halide of the formula

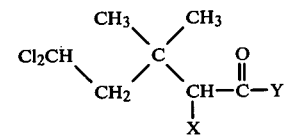

wherein X and Y each independently is a halogen atom, with a base selected from the group consisting of an alkali metal hydroxide, alkaline earth metal hydroxide, tertiary amine, alkali metal carbonate and alkaline earth metal carbonate in the presence of water, thereby to form a salt of the formula

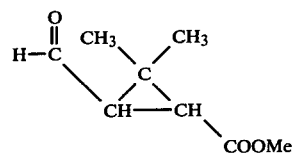

in which Me is an equivalent of an alkali metal, alkaline earth metal or ammonium cation, and then acidifying to replace Me by H.

* * * * *